United States Patent
Nolte et al.

(10) Patent No.: US 9,818,164 B2
(45) Date of Patent: Nov. 14, 2017

(54) FACILITATING AND TRACKING CLINICIAN-ASSIGNMENT STATUS

(75) Inventors: Mark Allen Nolte, Lee's Summit, MO (US); Rajneesh Mehra, Overland Park, KS (US); Brice McIver, Kansas City, MO (US); Terng Lim, Kansas City, MO (US); Eric Kays, Olathe, KS (US); Henri McCracken, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 509 days.

(21) Appl. No.: 13/236,339

(22) Filed: Sep. 19, 2011

(65) Prior Publication Data

US 2012/0253836 A1    Oct. 4, 2012

Related U.S. Application Data

(63) Continuation-in-part of application No. 12/567,174, filed on Sep. 25, 2009.

(51) Int. Cl.
  *G06Q 50/22*   (2012.01)
  *G06Q 50/24*   (2012.01)
  *G06Q 10/10*   (2012.01)

(52) U.S. Cl.
  CPC ............. *G06Q 50/22* (2013.01); *G06Q 10/10* (2013.01)

(58) Field of Classification Search
  CPC .. G06F 19/3406; G06F 19/327; G06F 19/322; G06F 19/324; G06F 19/3418; G06F 19/3437; G06F 19/3462; G06F 19/3468; G06F 19/3481; G06Q 50/22; G06Q 50/24; G06Q 10/10; G06Q 10/06

USPC ......................................................... 705/2, 3
See application file for complete search history.

(56) References Cited

U.S. PATENT DOCUMENTS

| | | |
|---|---|---|
| 5,966,692 A | 10/1999 | Langer et al. |
| 7,444,291 B1 | 10/2008 | Prasad et al. |
| 7,716,072 B1 | 5/2010 | Green, Jr. et al. |
| 2002/0013516 A1 | 1/2002 | Freyre et al. |
| 2003/0140928 A1 | 7/2003 | Bui et al. |
| 2004/0039602 A1 | 2/2004 | Greenberg et al. |

(Continued)

OTHER PUBLICATIONS

Non-Final Office Action dated Dec. 9, 2010 re U.S. Appl. No. 12/347,475, filed Dec. 31, 2008, 10 pages.

(Continued)

*Primary Examiner* — Maroun Kanaan
(74) *Attorney, Agent, or Firm* — Shook, Hardy & Bacon L.L.P.

(57) ABSTRACT

Subject matter described herein is related to assigning a healthcare clinician to provide care to a patient. For example, a GUI is provided that includes contextual information relevant to the assignment and that allows a user to electronically create the assignment. Relevant information includes a list of clinicians, a list of patients, and an estimate of the amount of resources required to provide care to a patient. In addition, this disclosure describes tracking the status of a healthcare clinician, such as primary provider, secondary provider, and on-break. Status might be tracked by capturing an image of a display board, which supports clinician barcodes that are movable to desired locations within a depiction of a healthcare facility (e.g., floor plan laid out using barcodes).

5 Claims, 10 Drawing Sheets

(56) References Cited

U.S. PATENT DOCUMENTS

| | | | |
|---|---|---|---|
| 2004/0176667 A1 | 9/2004 | Mihai et al. | |
| 2005/0075904 A1* | 4/2005 | Wager et al. | 705/2 |
| 2006/0047538 A1 | 3/2006 | Condurso et al. | |
| 2006/0069717 A1 | 3/2006 | Mamou | |
| 2008/0015903 A1 | 1/2008 | Rodgers | |
| 2008/0046292 A1 | 2/2008 | Myers et al. | |
| 2008/0077447 A1 | 3/2008 | Jung et al. | |
| 2008/0126126 A1 | 5/2008 | Ballai | |
| 2009/0119124 A1 | 5/2009 | Kambaloor | |
| 2009/0182594 A1 | 7/2009 | Choubey | |
| 2009/0204434 A1 | 8/2009 | Breazeale, Jr. | |
| 2010/0010859 A1* | 1/2010 | Ratakonda et al. | 705/9 |
| 2011/0001605 A1* | 1/2011 | Kiani et al. | 340/5.6 |
| 2011/0054936 A1* | 3/2011 | Cowan et al. | 705/3 |
| 2013/0096936 A1 | 4/2013 | Sampath et al. | |

OTHER PUBLICATIONS

Final Office Action dated Aug. 5, 2011 re U.S. Appl. No. 12/347,475, filed Dec. 31, 2008, 14 pages.
Non-Final Office Action dated Dec. 23, 2010 re U.S. Appl. No. 12/347,487, filed Dec. 31, 2008, 10 pages.
Final Office Action dated Jul. 13, 2011 re U.S. Appl. No. 12/347,487, filed Dec. 31, 2008, 14 pages.
Non Final Office Action of U.S. Appl. No. 12/567,956, dated Jan. 18, 2012, 9 pages.
Non Final Office Action of U.S. Appl. No. 12/567,174, dated Jan. 19, 2012, 9 pages.
Final Office Action in U.S. Appl. No. 12/567,174, dated Jul. 31, 2012, 12 pages.
Final Office Action in U.S. Appl. No. 12/567,956, dated Sep. 25, 2012, 12 pages.
Non Final Office Action in U.S. Appl. No. 12/567,956, dated Apr. 10, 2013, 10 pages.
Non Final Office Action in U.S. Appl. No. 12/567,174, dated Sep. 11, 2013, 22 pages.
PreInterview First Action Interview in U.S. Appl. No. 13/236,343, dated Oct. 22, 2013, 14 pages.
Non Final Office Action in U.S. Appl. No. 12/567,956, dated Apr. 25, 2014, 26 pages.
Final Office Action in U.S. Appl. No. 12/567,956, dated Nov. 19, 2013, 11 pages.
Non-Final Office Action dated Jun. 19, 2014 in U.S. Appl. No. 12/347,487, 14 pages.
Non-Final Office Action dated Jul. 7, 2014 in U.S. Appl. No. 12/567,174, 11 pages.
Non-Final Office Action dated Jul. 18, 2014 in U.S. Appl. No. 12/347,475, 13 pages.
Non-Final Office Action dated Sep. 22, 2014 in U.S. Appl. No. 13/236,343, 11 pages.
Non-Final Office Action dated Jan. 2, 2015 in U.S. Appl. No. 12/567,956, 9 pages.
Final Office Action dated Mar. 17, 2015 in U.S. Appl. No. 12/347,475, 16 pages.
Non-Final Office Action dated Mar. 13, 2015 in U.S. Appl. No. 12/347,487, 16 pages.
Final Office Action dated Mar. 27, 2015 in U.S. Appl. No. 12/567,174, 11 pages.
Final Office Action dated Jun. 11, 2015 in U.S. Appl. No. 13/326,343, 5 pages.
Final Office Action dated Sep. 10, 2015 in U.S. Appl. No. 12/567,956, 10 pages.
Non-Final Office Action dated Dec. 30, 2015 in U.S. Appl. No. 12/347,487, 16 pages.
Non-Final Office Action dated Jan. 7, 2016 in U.S. Appl. No. 12/567,174, 14 pages.
Non-Final Office Action dated Feb. 12, 2016 in U.S. Appl. No. 13/236,343, 6 pages.
Non-Final Office Action dated Mar. 11, 2016 in U.S. Appl. No. 12/567,956, 12 pages.
Final Office Action dated May 31, 2016 in U.S. Appl. No. 13/236,343, 7 pages.
Final Office Action dated Jul. 15, 2016 in U.S. Appl. No. 12/347,487, 23 pages.

* cited by examiner

FACILITATING AND TRACKING CLINICIAN-ASSIGNMENT STATUS

CROSS REFERENCE TO RELATED APPLICATIONS

This application is a continuation-in-part of U.S. patent application Ser. No. 12/567,174, which was filed on Sep. 25, 2009. U.S. patent application Ser. No. 12/567,174 is incorporated herein by reference in its entirety. In addition, the application is related to U.S. application Ser. No. 13/236,343, entitled GAUGING RESOURCE INTENSIVENESS OF PROVIDING CARE TO A PATIENT, which is filed on an even date herewith, and is incorporated herein by reference in its entirety.

BACKGROUND

In a healthcare environment, the responsibilities of a clinician (e.g., nurse) are often defined before the clinician begins to work a designated shift. For example, when working, a nurse is often assigned as either a primary caregiver or a secondary caregiver of a group of patients, and this group of patients is determined prior to beginning the designated shift.

However, typically these assignments are manually determined and made independently of relevant information (e.g., electronic scheduling system). For example, once a paper assignment sheet is manually filled out (e.g., by a nurse manager) to specify patient-caregiver assignments, the assignments must be manually entered into other healthcare electronic systems. In addition, when created independently of other systems, the assignments are made without access to relevant information (e.g., how much time is required to provide care to a patient).

SUMMARY

A high-level overview of various aspects of the invention is provided here for that reason, to provide an overview of the disclosure and to introduce a selection of concepts that are further described in the detailed-description section below. This summary is not intended to identify key features or essential features of the claimed subject matter, nor is it intended to be used as an aid in isolation to determine the scope of the claimed subject matter.

In brief and at a high level, this disclosure describes, among other things, providing contextual information that is relevant to assigning a healthcare clinician to a patient. Moreover, this disclosure describes suggesting an assignment of a clinician to a patient based on the contextual information. In addition, this disclosure describes, making assignment information available to other systems within a healthcare facility.

Subject matter described herein is also related to estimating a quantity of resources that are consumed or expended when providing care to a patient. When estimating the quantity, nonclinical information might be used to draw various inferences. For example, information provided by a real-time-location-service system might provide insight (e.g., duration, frequency, etc.) into instances in which a healthcare clinician visits a patient's room. In another example, information provided by a medical-device alarm system might provide insight into alarms that are triggered by equipment that monitors and/or provides assistance to a patient.

BRIEF DESCRIPTION OF THE SEVERAL VIEWS OF THE DRAWINGS

Illustrative embodiments of the present invention are described in detail below with reference to the attached drawing figures, wherein.

DETAILED DESCRIPTION

The subject matter of select embodiments of the present invention is described with specificity herein to meet statutory requirements. But the description itself is not intended to define what is regarded as our invention, which is what the claims do. The claimed subject matter might be embodied in other ways to include different steps or combinations of steps similar to the ones described in this document, in conjunction with other present or future technologies. Terms should not be interpreted as implying any particular order among or between various steps herein disclosed unless and except when the order of individual steps is explicitly stated.

An embodiment of the present invention is directed to assigning a healthcare clinician to provide care to a patient. For example, a list of healthcare clinicians that are scheduled to work during an upcoming shift is displayed together with contextually relevant information. An example of contextually relevant information includes a resource-consumption score, which suggests a relative amount of healthcare resources expended to provide care to the patient. A user (e.g., nurse manager who is determining patient assignments) can consider the contextually relevant information when making a determination as to which healthcare clinician should be assigned to provide care to the patient. Another embodiment is directed to calculating a resource-consumption score of a patient. A further embodiment is directed to making the assignment of a healthcare clinician known (or at least discoverable) to other systems of the healthcare facility.

Figure 1:
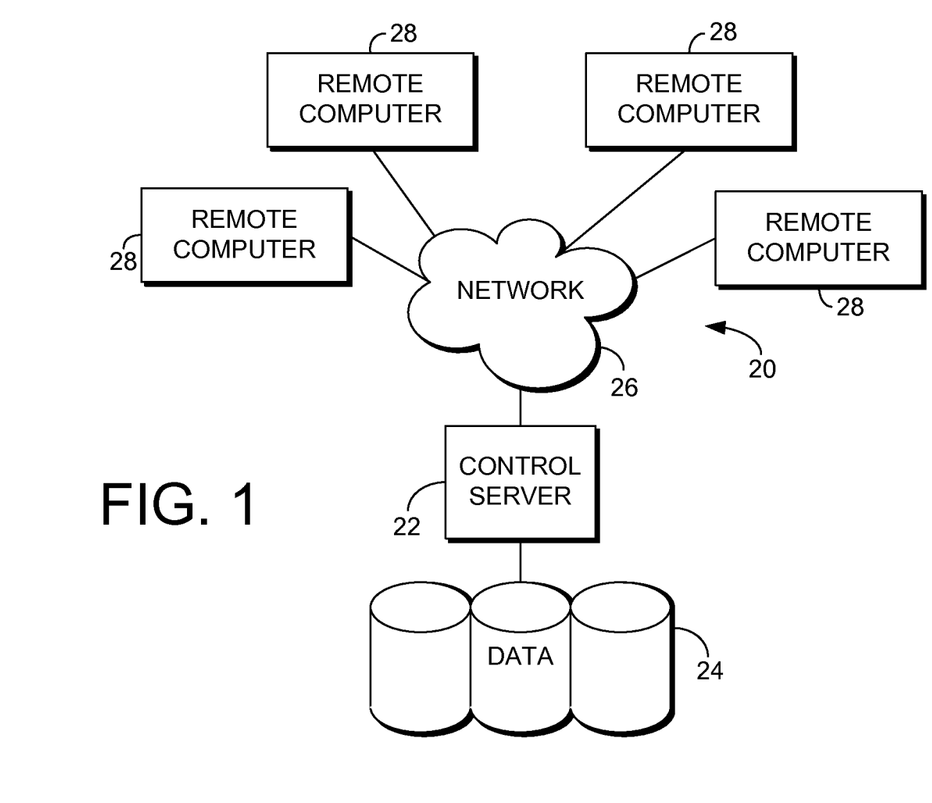
FIGS. 1 and 2 depict exemplary computing environments.

Having briefly described embodiments of the present invention, an exemplary operating environment suitable for use in implementing embodiments of the present invention is described below. Referring to FIG. 1 an exemplary computing environment (e.g., medical-information computing-system environment) with which embodiments of the present invention might be implemented is illustrated and designated generally as reference numeral 20. The computing environment 20 is merely an example of one suitable computing environment and is not intended to suggest any limitation as to the scope of use or functionality of the invention. Neither should the computing environment 20 be interpreted as having any dependency or requirement relating to any single component or combination of components illustrated therein.

The present invention might be operational with numerous other general purpose or special purpose computing system environments or configurations. Examples of well-known computing systems, environments, and/or configurations that might be suitable for use with the present invention include personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules include routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 20 includes a general purpose computing device in the form of a control server 22. Exemplary components of the control server 22 include a processing unit, internal system memory, and a suitable system bus for coupling various system components, including datastore cluster 24, with the control server 22. The system bus might be any of several types of bus structures, including a memory bus or memory controller, a peripheral bus, and a local bus, using any of a variety of bus architectures. Exemplary architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, datastore cluster 24. Computer-readable media can be any available media that might be accessed by server 22, and includes volatile and nonvolatile media, as well as, removable and nonremovable media.

Computer-readable media might include computer storage media. Computer storage media includes volatile and nonvolatile media, as well as, removable and nonremovable media implemented in any method or technology for storage of information, such as computer-readable instructions, data structures, program modules, or other data. In this regard, computer storage media might include RAM, ROM, EEPROM, flash memory or other memory technology; CD-ROM, digital versatile disks (DVDs) or other optical disk storage; magnetic cassettes, magnetic tape, magnetic disk storage, or other magnetic storage device; or any other tangible storage medium which can be used to store the desired information and which may be accessed by the control server 22. Combinations of any of the above also may be included within the scope of computer-readable media.

Computer-readable media can also include communications media, which typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, communication media includes wired media, such as a wired network or direct-wired connection, and wireless media, such as acoustic, RF, infrared and other wireless media. Combinations of any of the above should also be included within the scope of computer-readable media.

The computer storage media discussed above and illustrated in FIG. 1, including datastore cluster 24, provide storage of computer-readable instructions, data structures, program modules, and other data for the control server 22.

The control server 22 might operate in a computer network 26 using logical connections to one or more remote computers 28. Remote computers 28 might be located at a variety of locations in a medical or research environment, including clinical laboratories (e.g., molecular diagnostic laboratories), hospitals, and other inpatient settings, veterinary environments, ambulatory settings, medical billing and financial offices, hospital administration settings, home healthcare environments, and clinicians' offices. Clinicians might include a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 28 might also be physically located in nontraditional medical care environments so that the entire healthcare community might be capable of integration on the network. The remote computers 28 might be personal computers, servers, routers, network PCs, peer devices, other common network nodes, or the like and might include some or all of the elements described above in relation to the control server 22. The devices can be personal digital assistants or other like devices.

Exemplary computer networks 26 include local area networks (LANs) and/or wide area networks (WANs). Such networking environments are commonplace in offices, enterprise-wide computer networks, intranets, and the Internet. When utilized in a WAN networking environment, the control server 22 might include a modem or other means for establishing communications over the WAN, such as the Internet. In a networked environment, program modules or portions thereof might be stored in association with the control server 22, the datastore cluster 24, or any of the remote computers 28. For example, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) might be utilized.

In operation, a clinician might enter commands and information into the control server 22 or convey the commands and information to the control server 22 via one or more of the remote computers 28 through input devices, such as a keyboard, a pointing device (commonly referred to as a mouse), a trackball, or a touch pad. Other input devices include microphones, satellite dishes, scanners, or the like. Commands and information might also be sent directly from a remote healthcare device to the control server 22. In addition to a monitor, the control server 22 and/or remote computers 28 might include other peripheral output devices or presentation devices, such as speakers and a printer.

Although many other internal components of the control server 22 and the remote computers 28 are not shown, those of ordinary skill in the art will appreciate that such components might be included.

Figure 2:
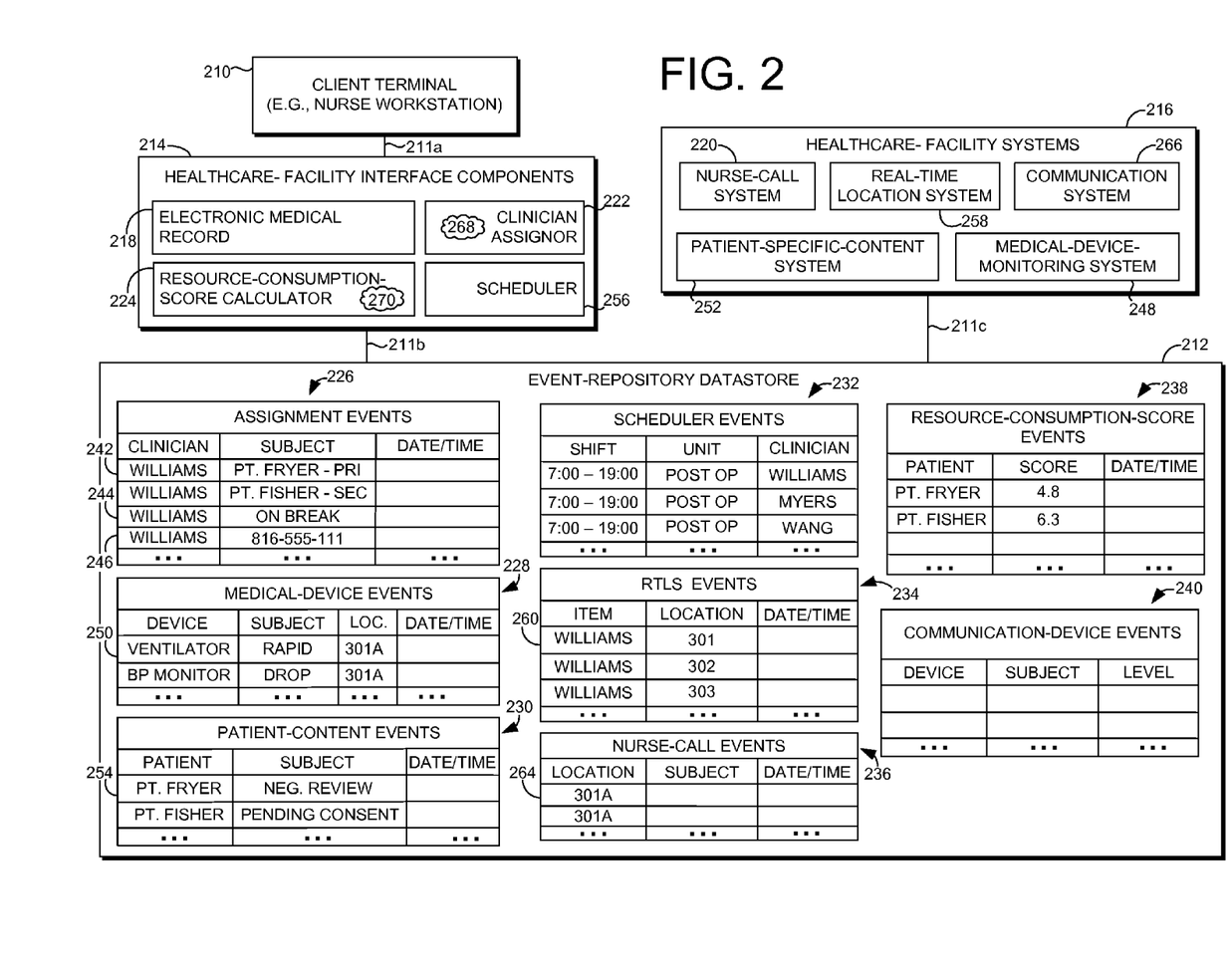

Turning now to FIG. 2, another diagram depicts various components that might be found in the environment shown in FIG. 1. FIG. 2 includes a client terminal 210 and an event-repository datastore 212. In addition, FIG. 2 includes a collection of components 214 labeled as "Healthcare-Facility Interface Components" and another collection of items 216 labeled as "Healthcare-Facility Systems." Each of these items will be briefly described to provide some context and then will be described in more detail hereinafter.

Generally, a user (e.g., nurse or other clinician) uses client terminal 210 to access various information, such as an electronic medical record, a list of scheduled healthcare clinicians, a list of medical-device alerts, and a list of clinician assignments. (Other information is also accessible, but is not described in the context of this subject matter.) Such information is accessible using the various components listed in collection 214. Components in collection 214 might be running directly on client terminal 210 or might be accessed over a network (represented by reference numerals 211a-c). For example, a user might log-on to client terminal 210 to access an electronic medical record of a patient by using the electronic medical record component 218. In such an example, client terminal 210 might be a remote computer 28 of FIG. 1, and the electronic medical record might either be stored in memory of the client terminal or in data 24 of FIG. 1. Accordingly, each of the interface components listed among collection 214 includes a combination of hardware and software that provide certain functionality (as will be described in more detail hereinafter) to client terminal 210, thereby allowing the client terminal to access certain information.

Interface components 214 might consume (i.e., retrieve and leverage) information stored in datastore 212 for various purposes, such as to provide access to the retrieved information or to use the retrieved information to generate additional data. That is, when generating and providing requested information to client terminal 210, an interface component might retrieve information from datastore 212. For example, scheduler 256 or assignor 222 might retrieve data from scheduler events 232 to enable a user to view the data using client terminal 210.

In addition to retrieving information stored in datastore 212, interface components 214 might push events to datastore 212, such that the events can be stored for consumption by other systems and programs. For example, if an assignment is made using clinician assignor 222, assignment information might be sent to datastore 212 to be used by electronic medical record 218 or by nurse call system 220.

Systems 216 also provide information (e.g., event notifications) to datastore 212 to be consumed by other applications and systems used in a healthcare environment. For example, nurse call system 220 might provide a notification to datastore 212 indicting that a nurse call was submitted by a patient in room 102. That information can then be retrieved by other systems, such as resource-consumption-score calculator 224.

Accordingly, datastore 212 functions as a repository of information that can be leveraged by various components in a healthcare facility. In one embodiment, events are stored using components and methods described in U.S. patent application Ser. No. 12/567,174, which is incorporated herein by reference in its entirety. Datastore might be a component of client terminal 210 or might be networked with client terminal 210. Datastore 212 depicts various categories of "events" that are meant to be illustrative; however, datastore 212 might also store various other categories of events that are not depicted. Illustrative events include assignment events 226, medical-device events 228, patient-content events 230, scheduler events 232, real-time location system (RTLS) events 234, nurse-call events 236, resource-consumption-score events 238, and communication-device events 240.

Assignment events 226 are received from clinician assignor 222 and might indicate a variety of information. For example, when clinician assignor 222 is used to assign a healthcare clinician to a patient as either a primary caregiver or a secondary caregiver, that assignment event is sent to datastore 212. Entry 242 represents an example of information that is received as a result of an assignment event. Likewise, when a clinician goes on break, that information is also tracked as depicted by entry 244. In addition, an assignment of a clinician to a communications device (e.g., in-house phone or pager) might also be stored as indicated by entry 246.

Medical-device events 228 are received from medical-device-monitoring system 248. That is, medical-device-monitoring system 248 includes various medical devices that are used to monitor and/or administer care to a patient, such as an oxygen monitor, an infusion pump, a cardiac ventilator, a balloon pump, a patient bed, and vital-sign detecting devices. As such, these medical devices generate various data (e.g., heart-rate changes) that is communicated to datastore 212. Exemplary data includes those entries indicated at reference numeral 250.

Patient-content events 230 are received from patient-specific-content system 252, which includes both a patient-interactive computing device (e.g., bedside computing device used by the patient) and content (e.g., surveys, lunch menu, advertisements, consent forms, educational materials, etc.) that are provided to the patient via the patient-interactive computing device. For example, a patient might be provided with a survey that is completed by the patient using the patient-interactive computing device positioned at a patient's bedside. Information gathered from the patient (e.g., nurse ratings) via the survey is sent to datastore 212 as indicated by entry 254, which reads "neg. review."

Scheduler events 232 are received from scheduler 256. For example, scheduler 256 is accessed (e.g., from client terminal 210) to electronically create a schedule that designates when a healthcare clinician is selected to work at a healthcare facility. As such, scheduler 256 can send shift information to datastore 212 that identifies a list of healthcare clinicians scheduled to work in a healthcare-facility unit during a designated shift (e.g., 7:00 to 19:00). The scheduler events can then be stored in datastore 212.

Real-time-location-system (RTLS) events 234 are received from real-time location system 258 (RTLS) and indicate locations within a healthcare facility at which a tracked object is detected. Exemplary tracked objects include nurses, patients, and medical devices. Often objects are tracked using a signal receiver that detects a signal emitted by a signal transmitter. The signal may be encoded to include unique information that identifies a tracked object to which the signal transmitter is attached. For example, a signal receiver might be positioned in a known location (e.g., patient room) and operate to detect signals emitted by various signal transmitters that are attached to tracked objects. Because the signal may include information that is unique to (i.e., identifies) a tracked object, the RTLS may deem that the tracked object was near the known location. Alternatively, signal transmitters might be positioned in a known location and operate to emit a signal that is detected by a signal receiver attached to a tracked object. For example, RTLS 258 might include a series of RFID tag readers that are placed throughout the healthcare facility, such as in patient rooms, common areas, break rooms, and hallways. Accordingly, because tracked objects include an RFID tag that emits a signal having information unique to the tracked object, the RFID tag reader can detect a presence of a tracked object in a particular area. Other signaling technologies might also be used, such as Wi-Fi or other wireless-signal technologies. RTLS 258 typically includes an application that allows a user, such as through client terminal 210, to determine a detected location of a tagged object. In addition, RTLS 258 provides presence-event information (e.g., detection of a staff member in patient room) to datastore 212 as depicted by entry 260

Nurse-call events 236 are received from nurse-call system 220, such as when a patient requests assistance. That is, often a patient will request a clinician's presence via nurse-call system 220. Accordingly, nurse-call system 220 might send a nurse-call event notification in parallel to datastore 212. Entry 264 is provided for illustrative purposes and includes the location from which a nurse-call request is sent.

Resource-consumption-score events 238 are received from resource-consumption-score calculator 224. For example, resource-consumption-score calculator 224 might generate a resource-consumption score, which suggests a relative amount of healthcare resources expended to provide care to a patient. Accordingly, when the score is generated, in addition to providing the score to other applications or systems, resource-consumption-score calculator 224 might also send the score to datastore 212.

Communication-device events 240 are received from communication system 266. For example, communication system 266 might include several communication devices, such as in-house phones or pagers, that are distributed among healthcare clinicians and that receive alerts and other messages. Accordingly, when a message is sent to a particular communication device, communication system 266 also provides an event notification to datastore 212. An exemplary event notification from communication system 266 might include various information such as the device to which an alert was sent, a description of the alert, and the severity level of the alert.

Figure 3:
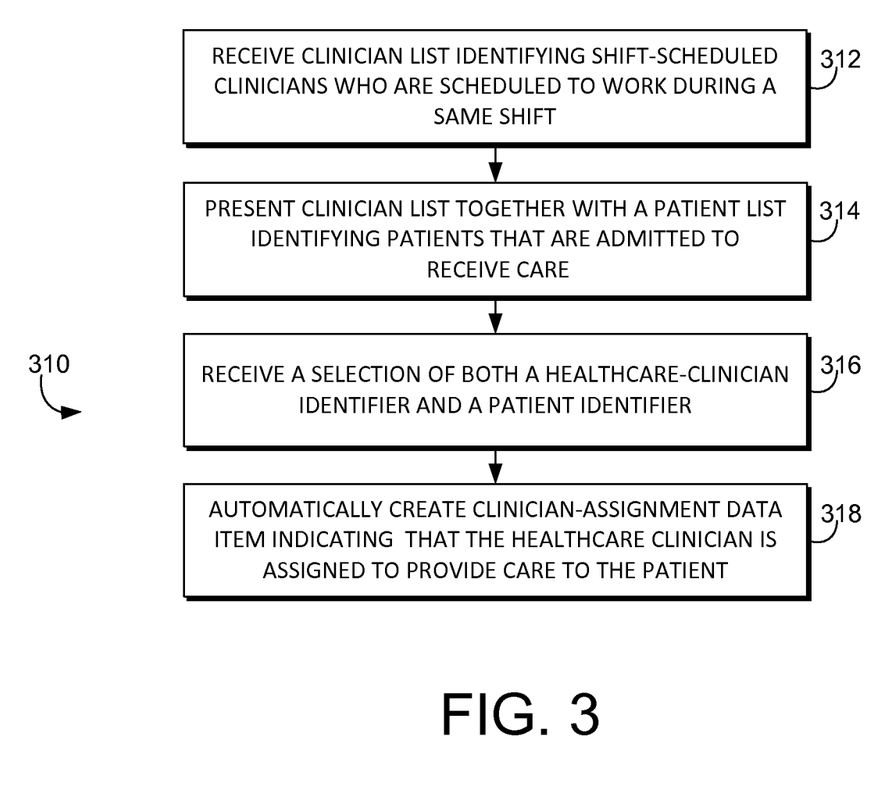
FIGS. 3, 5, 8, 9, and 10 each depict a flow diagram of a method.

Referring now to FIG. 3, a flow diagram depicts a method 310 of assigning a healthcare clinician to provide care to a patient. When describing FIG. 3, reference might also be made to other figures of the instant application, such as FIGS. 2 and 4. In order to assign a clinician to provide care to a patient, a user (e.g., nurse manager) of client terminal 210 might use clinician assignor 222, which includes an application 268. As described previously, application 268 might be running directly on terminal 210 or might be accessible over a network 211a-c. Furthermore, the steps depicted in FIG. 3 might include computer-executable instructions that, when executed by a computing device, facilitate method 310.

At 312, method 310 includes receiving a clinician list identifying one or more shift-scheduled clinicians who are scheduled to work during a same shift. For example, clinician assignor 222 might request and receive a list of clinicians from scheduler events 232, which is maintained in datastore 212. When clinician assignor 222 requests the list of clinicians, clinician assignor 222 might specify a date and shift (e.g., 7:00-19:00), such that clinician assignor 222 queries datastore 212 to receive schedule information.

Clinician assignor 222 might receive the list when a user starts an instance of application 268, such as part of a loading process of application 268. Alternatively, the list might be sent to clinician assignor 222 at regular intervals (e.g., every eight hours), or might be automatically forwarded to clinician assignor 222 when it is created (i.e., when a schedule is completed using scheduler 256). Scheduler events 232 depicts that an identifier (e.g., name, unique number, etc.) is included in scheduling information so as to identify a clinician that is scheduled to work during a particular shift.

Figure 4:
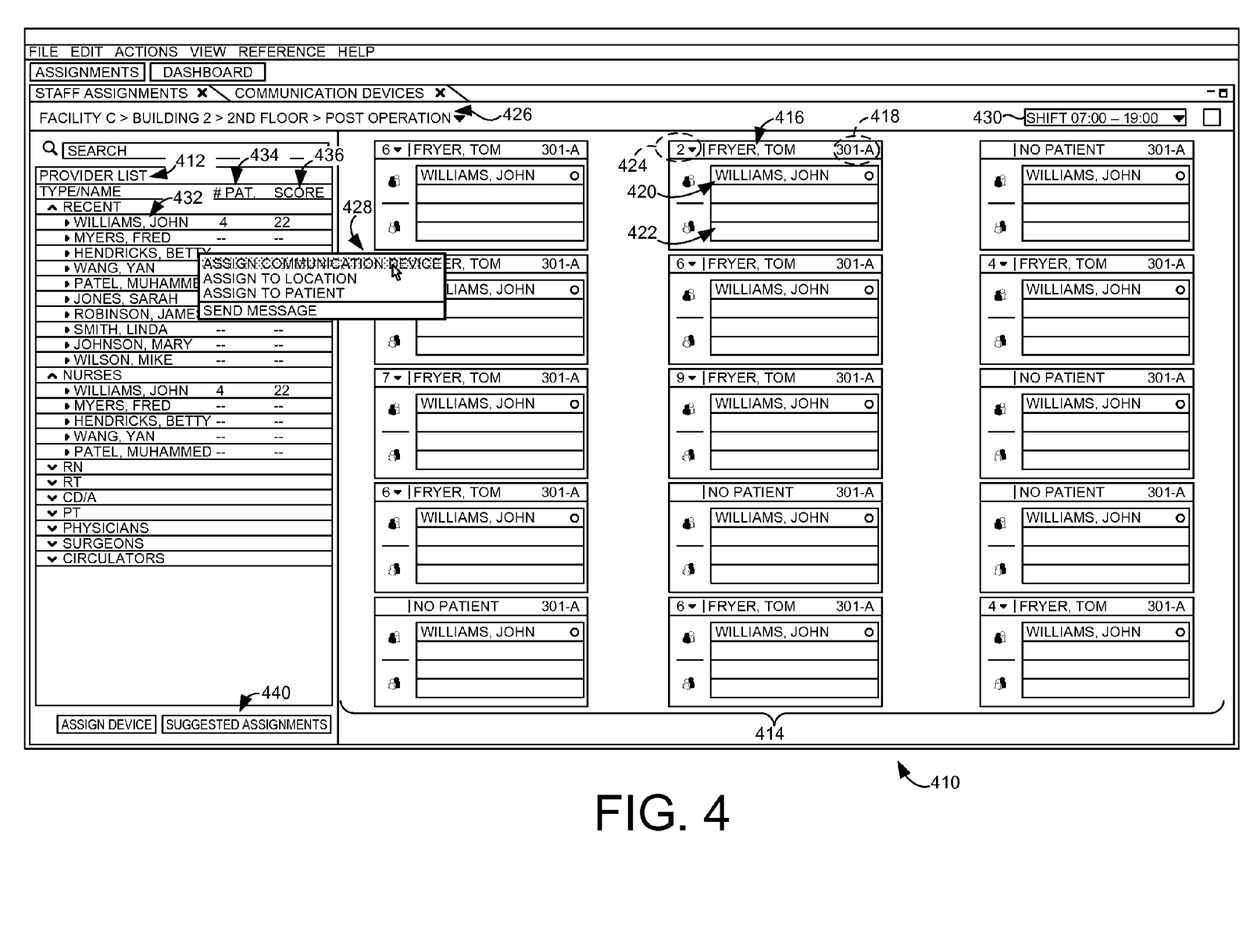
FIG. 4 depicts an exemplary screenshot.

Method 310 also includes step 314, which includes presenting the clinician list in a graphical user interface (GUI) together with a patient list identifying one or more patients that are admitted to receive care. For example, FIG. 4 illustrates a screen shot 410 depicting a graphical user interface ("GUI"). Screen shot 410 includes a clinician list 412 that is identified as "Provider List." Moreover, screen shot 410 includes a list of patients 414, which is presented in a grid-like arrangement to the right of the clinician list. That is, the grid-like arrangement includes a series of boxes that are arranged into columns and rows. Each box includes a patient identifier 416 (e.g., name), a room number 418 (e.g., 301-A), a primary-provider entry field 420, a secondary-provider entry field 422, and a resource-consumption score 424.

Screenshot 410 includes other contextual information that can be insightful when assigning responsibilities to a clinician. For example, screen shot 410 identifies a unit 426 (e.g., post operation) for which the assignments are made. In addition, screenshot 410 depicts a pop-up box 428 that can be invoked, such as by right clicking a mouse (or a variety of other mouse or keyboard actions) when a cursor is positioned over a clinician name. Pop-up box 428 allows additional actions to be taken with respect to a clinician, such as assigning a communications device (e.g., in-house phone or pager) or assigning a patient.

Screenshot 410 also includes a shift-selection box 430, which depicts a shift (e.g., 7:00-19:00) for which assignments are being made. In an embodiment, a different provider list can be retrieved from datastore 212 by selecting a different shift. For example, a drop-down menu might be used to specify a shift other than 7:00-19:00. In addition, screenshot 410 includes a number-of-patients column 434, which lists a number of patients that are currently assigned to a clinician (e.g., clinician John Williams is assigned to four patients).

Screenshot 410 also includes a score column 436, which lists a respective score of each clinician. A score of a clinician may quantify various conditions or factors that are taken into consideration when determining how much work a clinician is currently assigned and/or how much additional work a clinician can manage. For example, a score may comprise a workload score that reflects various clinical and non-clinical information, which is used to assess an amount of work assigned to a clinician. A score may also comprise an acuity score, which quantifies a level of difficulty associated with providing care to one or more patients. For example, when providing care to a certain patient is more demanding relative to providing care to other patients, that patient may be associated with a higher acuity score. Other factors that may be used to determine a score include patient assessment data, such as falls risk, isolation requirements, language barriers, bariatric patients, diet restrictions, NPO instruction (i.e., no oral food or fluids), etc. In addition to patient data, non-clinical data may be used to determine a clinician-workload score, such as a number of medical-device alarms or nurse-call alarms that are triggered during a shift, as well as RTLS events (e.g., a number of times a clinician enters a room during a shift). These are merely examples of types of data that may be used to determine a clinician workload and a variety of other factors may also be considered.

Step 316 includes receiving a selection via the GUI of both the identifier of the healthcare clinician and the identifier of the patient. For example, when interacting with the GUI depicted in screenshot 410, a user might operate a mouse or keyboard (e.g., tab function) to select the identifier 432 of clinician "John Williams." Once a clinician is selected, various actions might be taken to select a patient. For example, a mouse might be used to drag and drop a clinician identifier (e.g., the name "John Williams") onto a primary-provider entry field 420 or a secondary-provider entry field 422. Alternatively, various drop-down menus might be provided. For example, once a clinician is selected, a patient drop-down menu might be provided that lists patients assignable to the clinician. Or, a patient might be selected first, and a clinician drop-down menu provided that allows a clinician to be selected.

At step 318, in response to the selection of both the healthcare-clinician identifier and the patient identifier, a clinician-to-patient association is created that represents that the healthcare clinician is assigned to provide care to the patient. A clinician-to-patient association might include various embodiments of data stored in computer-storage media. For example, a clinician-to-patient association might include data stored in memory associated with application 268. In addition, the clinician-to-patient association might include data communicated to assignment events 226 in datastore 212, thereby allowing the association data to be consumed by other applications. In screenshot 410, the clinician-to-patient association is depicted by listing a clinician in a primary-provider entry field of a patient box, thereby indicating that the clinician is assigned to provide care to the patient.

Figure 5:
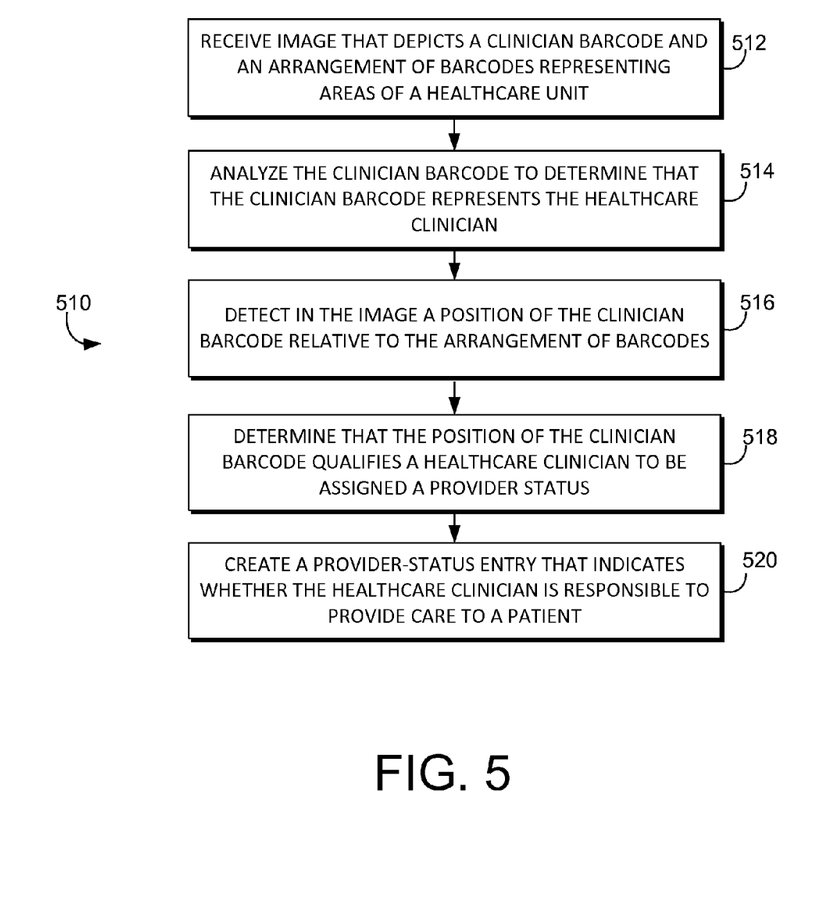

Referring now to FIG. 5, another flow diagram is shown that depicts a method 510 of assigning a provider status to a healthcare clinician, the provider status indicating whether the healthcare clinician is responsible to provide care to a patient. For example, a clinician might be designated as a primary care provider or a secondary care provider, each of which includes a respective set of responsibilities that the clinician must uphold with respect to the patient. In addition, even though a clinician might be assigned to a patient, the clinician might be unavailable to provide care (e.g., taking a break in the middle of a shift), and it is helpful to track such unavailability. As such, examples of a provider status include primary care provider, secondary care provider, and unavailable (e.g., on break).

Similar to method 310, method 510 might be carried out by application 268. Furthermore, the steps depicted in FIG. 5 might include computer-executable instructions that, when executed by a computing device, facilitate method 510. When describing FIG. 5, reference might also be made to FIGS. 2, 4, 6, and 7.

Figure 6:
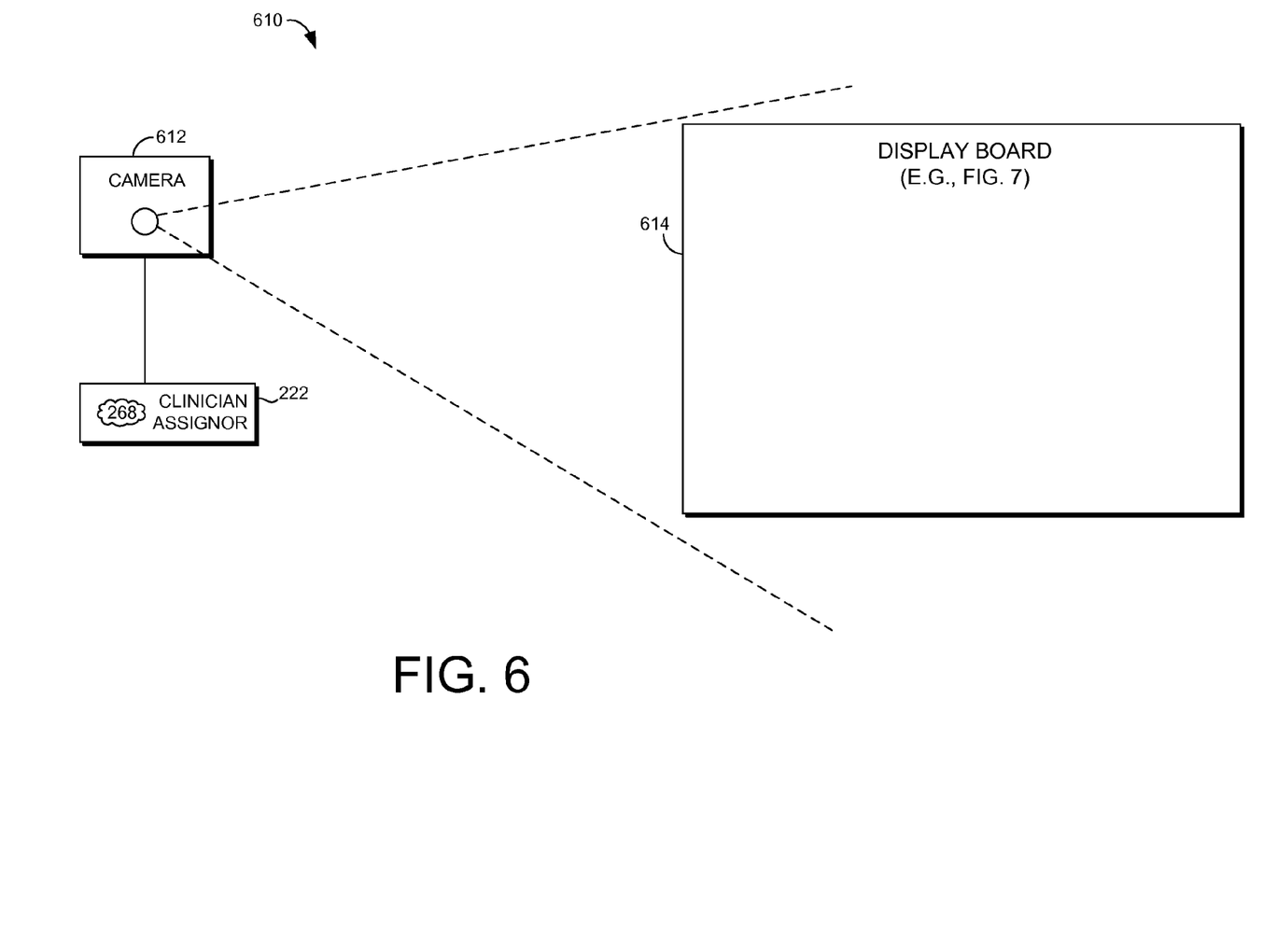
FIG. 6 depicts an exemplary image-capturing environment.

Pursuant to method 510, step 512 includes receiving an image that depicts a clinician barcode representing the healthcare clinician and that depicts an arrangement of barcodes representing one or more areas of a healthcare unit in which the healthcare clinician is scheduled to provide care. Pursuant to step 514, the clinician barcode is analyzed to determine that the barcode represents the clinician. For example, FIG. 6 illustrates an environment 610 in which a camera 612 is positioned to take a picture of a display board 614 (e.g., white board). In addition, camera 612 is linked to clinician assignor 222 having application 268. Accordingly, once an image (e.g., FIG. 7) is captured by camera 612, the image can be communicated to, and received by, clinician assignor 222.

Figure 7:
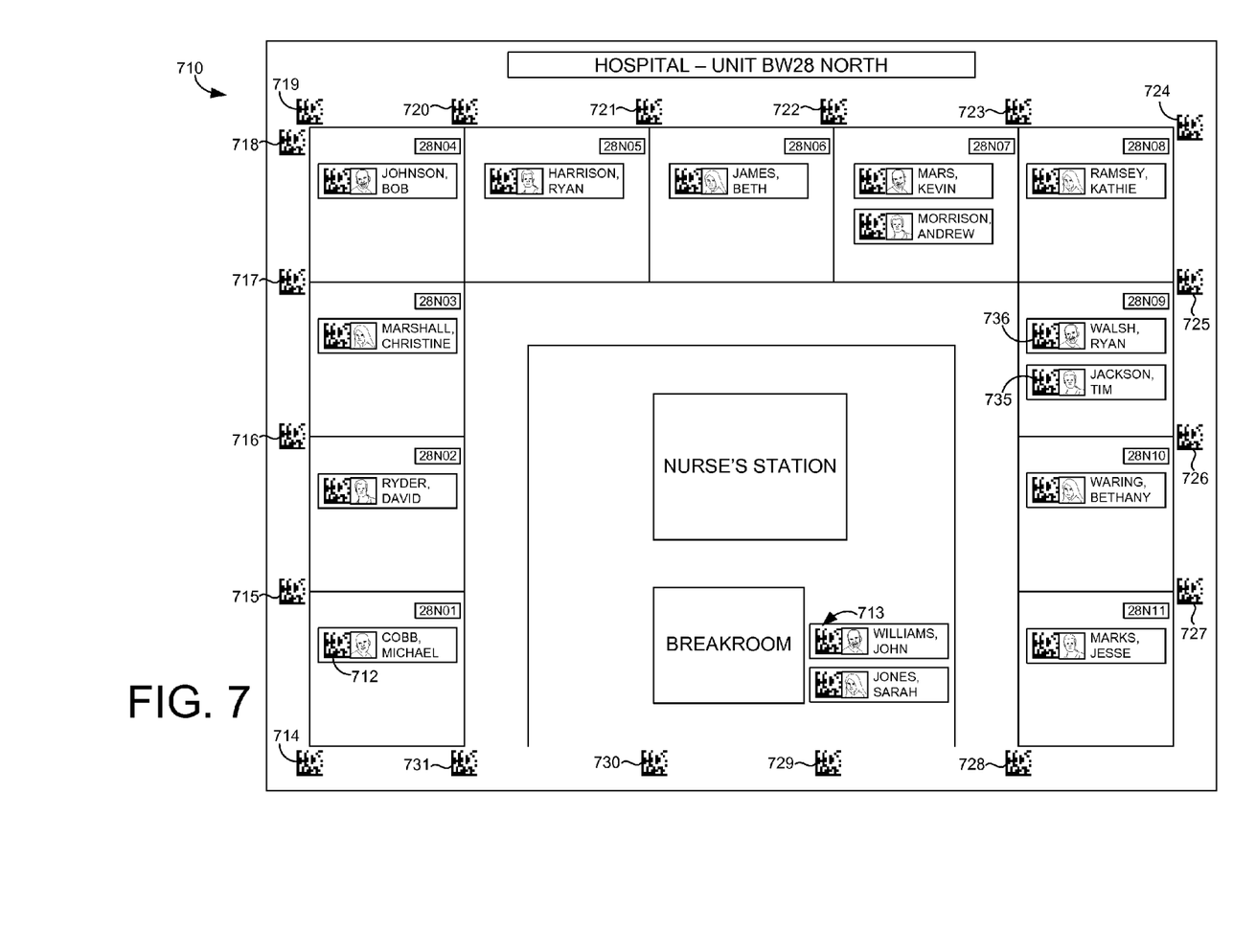
FIG. 7 depicts an exemplary display board.

FIG. 7 depicts an exemplary image 710. Image 710 depicts various clinician barcodes, such as clinician barcode 712. In addition, image 710 depicts an arrangement of barcodes 714-731 that represents areas of a healthcare unit (e.g., Unit BW28 North). For example, areas might include room 28N01-28N11 or might include a common area (e.g., nurse's station). In one embodiment barcodes 714-731 are arranged to depict an actual floor plan of the healthcare unit. The various barcodes depicted in FIG. 7 are removably attachable (e.g., using magnets) to the display board, such that the barcodes can be arranged in any desired configuration. Application 268 may include functionality to analyze (e.g., read or scan) the barcodes to determine information represented by a barcode and to determine a configuration in which barcodes are arranged. For example, a barcode may be analyzed to determine that the barcode represents a clinician. Moreover, barcodes may be analyzed to detect a floor-plan configuration and a position of a clinician barcode within the floor-plan configuration.

Step 516 includes detecting in the image a position of the clinician barcode relative to the arrangement of barcodes. For example, application 268 might detect a position of clinician barcode 712 or 713 relative to barcodes 714-731. At step 518, a determination is made that the position of the clinician barcode qualifies the healthcare clinician to be assigned the provider status. For example, a position of barcode 712 might qualify clinician "Michael Cobb" to be assigned as a primary care provider of a patient in room 28N01, and a position of barcode 713 might qualify clinician John Williams to be assigned an "on-break" or "unavailable" provider status. Other provider statuses are also assignable, such as a secondary care provider, which might be assigned when a barcode 735 is positioned below another barcode 736 within a detected patient room (e.g., 28N09).

Pursuant to method 510, step 520 includes creating a provider-status entry that indicates whether the healthcare clinician is responsible to provide care to the patient. Exemplary statuses in a provider-status entry that indicate a clinician's responsibility include primary care provider, secondary care provider, and on-break (or some other indication that a clinician is not responsible to provide care). Creating a provider-status entry might include various actions, such as storing the entry in a memory associated with application 268 or sending an event notification to assignment events 226. An exemplary provider-status entry is depicted by entry 244, which indicates that a clinician named "Williams" is on-break. In addition, a provider-status entry might be graphically depicted in a GUI, such as the GUI depicted by FIG. 4. For example, when a clinician is assigned as a primary care provider, the clinician's name might be displayed in a primary-provider entry field 420.

Figure 8:
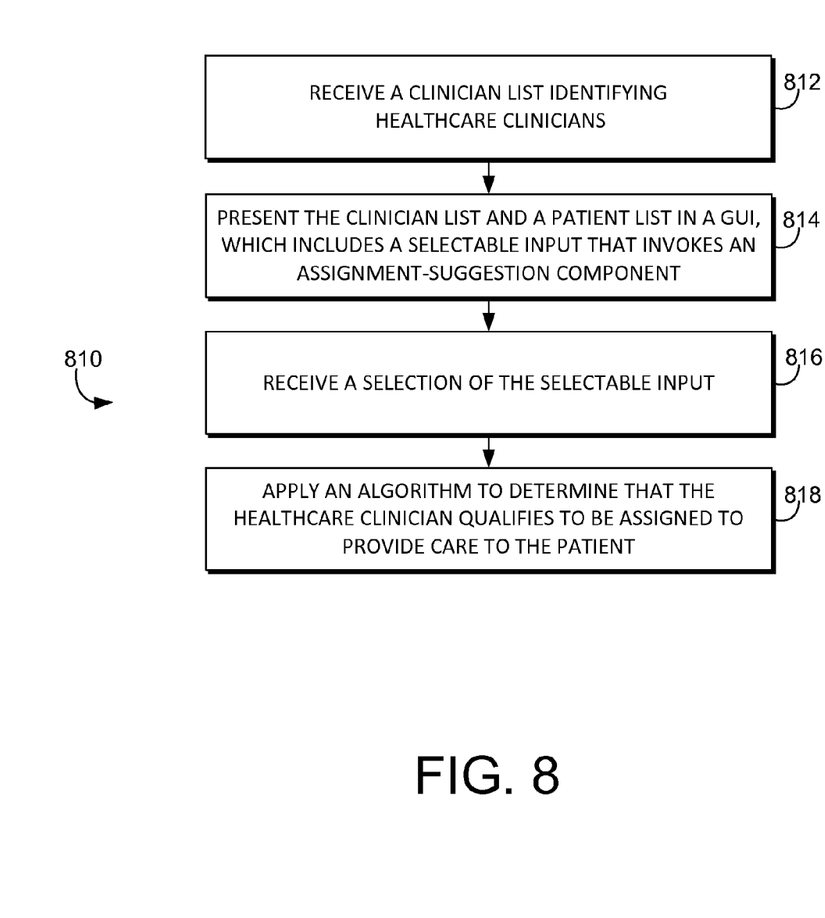

Referring now to FIG. 8, another flow diagram is shown that depicts a method 810 of assigning a healthcare clinician to provide care to a patient. Similar to method 310, method 810 might be carried out by application 268. Furthermore, the steps depicted in FIG. 8 might include computer-executable instructions that, when executed by a computing device, facilitate method 810. When describing FIG. 8, reference might also be made to FIGS. 2 and 4.

Pursuant to method 810, step 812 includes receiving a clinician list identifying one or more healthcare clinicians. This step is similar to step 312 described with respect to method 310 and FIG. 3. For example, clinician assignor 222 might request and receive a list of clinicians from scheduler events 232, which is maintained in datastore 212. When clinician assignor 222 requests the list of clinicians, clinician assignor 222 might specify a date and shift (e.g., 7:00-19:00), such that clinician assignor 222 queries datastore 212 to receive schedule information. Clinician assignor 222 might receive the list when a user starts an instance of application

268, such as part of a loading process of application 268. Alternatively, the list might be sent to clinician assignor 222 at regular intervals (e.g., every eight hours), or might be automatically forwarded to clinician assignor 222 when it is created (i.e., when a schedule is completed using scheduler 256). Scheduler events 232 depicts that an identifier (e.g., name, unique number, etc.) is included in scheduling information so as to identify a clinician that is scheduled to work during a particular shift.

Step 814 includes presenting the clinician list in a graphical user interface (GUI) together with a patient list identifying one or more patients. For example, screen shot 410 depicts clinician list 412 and patient list 414. Pursuant to method 810, the GUI includes a selectable input that, when selected, invokes an assignment-suggestion component. For example, screenshot 410 includes button 440 that reads "Suggested Assignments" and that can be selected, such as by using a mouse and cursor or a keyboard.

Step 816 includes receiving a selection via the GUI of the selectable input, and at step 818, in response to the selection, an algorithm is applied to determine that the healthcare clinician qualifies to be assigned to provide care to the patient. The algorithm might take various factors into consideration, such as a resource-consumption score (e.g., 424) of the patient.

As already described, a resource-consumption score suggests a relative amount of healthcare resources expended to provide care to the patient. That is, a resource-consumption score is a quantified measure of the resource intensiveness of providing care to a patient. For example, providing care to a patient might require a variety of different resources including multiple clinicians (e.g., nurses and physicians); durations of a clinician's time (i.e., long durations in which a clinician provides care to a patient and/or multiple instances at which a clinician provides care); and a particular clinician skill set or skill level. Accordingly, a resource-consumption score may represent a baseline metric that suggests a number of clinicians needed to provide care to a patient; an amount of clinician time needed to provide care to the patient; a frequency of clinician tasks that is required to provide care to the patient; a skill level of clinician(s) needed to provide care to the patient; and/or a total amount of clinician time needed to provide care to the patient. This resource intensiveness can be used to predict whether a clinician will have the capacity to care for a patient in an upcoming shift. In addition, resource-consumption scores can be normalized, thereby allowing one patient's score to be compared to a different patient's score.

A resource-consumption score might be retrieved from various sources, such as from resource-consumption-score events 238 in datastore 212 or directly from resource-consumption-score calculator 224. In one embodiment, the algorithm takes into consideration a summation of resource-consumption scores of all patients assigned to the healthcare clinician, in addition to a variety of other possible variables. For example, an acuity score displayed under column 436 might take into account a combination of resource-consumption scores, as well as other factors.

Resource-consumption-score calculator 224 ("calculator") might execute a series of instructions to determine a resource-consumption score based on various factors. Calculator 224 includes application 270 that executes various functions. For example, when calculating a resource-consumption score, nonclinical-information metrics might be retrieved from datastore 212 and used to determine a score. Nonclinical information generally describes conditions of a patient-care environment and of a patient-care experience, but does not specifically describe the patient or a condition of the patient. Examples of clinical information include demographic information (e.g., age, gender, weight, etc.) and diagnosis information (e.g., ailment, disease, etc.).

Metrics and data depicted in datastore 212 are examples of nonclinical information, such as a rating of the healthcare clinician submitted by the patient, a number of nurse-call events, a medical-device-alarm metric, a clinician-location metric, or a combination thereof. Although some forms of nonclinical information are not depicted by a single event entry, those forms are at least ascertainable from a collection of event entries. For example, by querying nurse-call events 236, a nonclinical-information metric that describes a number of times a patient initiated a nurse call during a shift can be calculated. In another example, RTLS events 234 can be queried to determine a number of times a clinician enters a patient's room during a shift or an amount of time spent by a clinician in a patient room during a shift.

Accordingly, nonclinical information that is used to calculate a resource-consumption score might be provided by various system or components depicted in FIG. 2. For example, nonclinical information might be provided by a patient-bedside entertainment and education system (i.e., patient-content system), nurse-call system, RTLS, communications system, and medical-device monitoring system.

Figure 9:
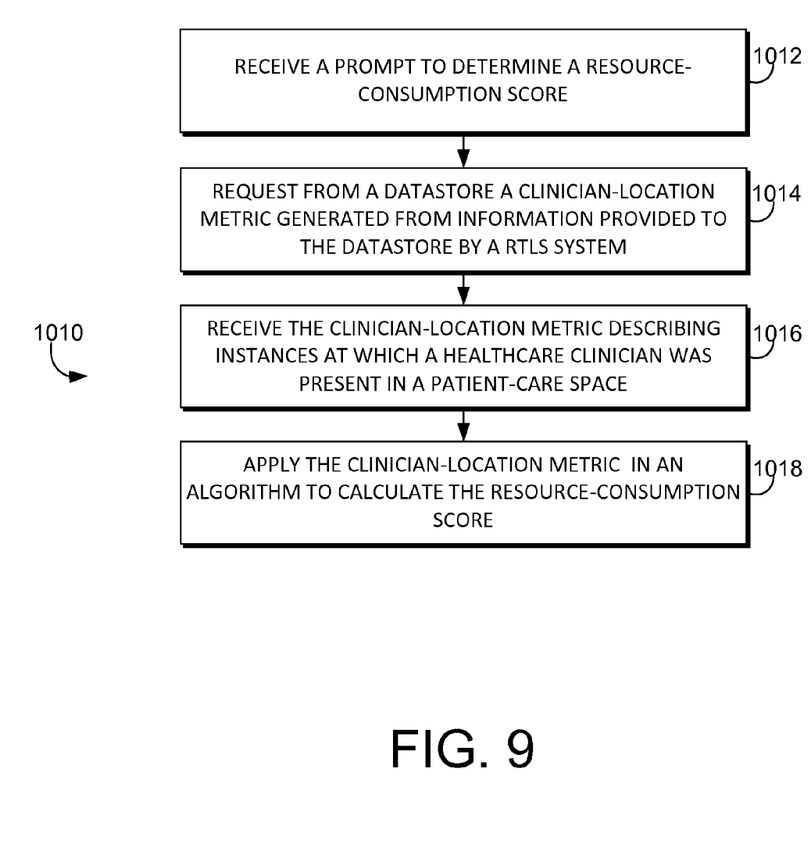

Calculator 224 and application 270 might operate in various scenarios, and reference is now made to FIG. 9, in which another flow diagram is depicted that walks through a method 1010 of determining a resource-consumption score that suggests a relative amount of healthcare resources expended to provide care to a patient. The steps depicted in FIG. 9 might include computer-executable instructions that, when executed by a computing device, facilitate method 1010. For example, the computer-executable instructions might be stored on computer-readable media and executed using application 270. When describing FIG. 9, reference might also be made to FIGS. 2 and 4.

As described in other portions of this description, an RTLS may include a signal receiver (e.g., RF receiver) that receives or detects a signal from a signal transmitter (e.g., RFID tag), the signal including information that is unique to or identifies a clinician. As such, the RTLS may match the information provided in the signal to a clinician and create a presence-event information item (e.g., 260), which indicates the clinician was detected in an area (e.g., patient-care space). The presence-event information item may then be consumed by other systems and processes. For example, step 1012 includes receiving a prompt to determine a resource-consumption score. A prompt might be received by calculator 224 when a user opens application 268, which enables the user to assign a clinician various responsibilities (e.g., primary care provider or secondary care provider). In addition, a prompt might be received when a user selects the input 440 titled "Suggested Assignments." In other embodiments, a user might interact directly with application 270 to request that a score be calculated. Moreover, a prompt might be received at time-based intervals (e.g., every 6, 8, and/or 12 hours).

At step 1014, method 1010 includes requesting from a datastore a clinician-location metric, which is generated from information (e.g., presence-event information item) that is provided to the datastore by a real-time location system (RTLS). For example, application 270 might query RTLS events to retrieve a clinician-location metric, and as explained previously, RTLS events 234 are provided to datastore 212 by RTLS 258.

A clinician-location metric can provide insight into where a clinician spends time working (e.g., providing patient care) during a period of time (e.g., a shift) and into how much time a clinician spends in various locations during a period of time. For example, a clinician-location metric might include a clinician-detection count, which indicates a number of times the RTLS detected a presence of the clinician in a patient-care space (e.g., patient room 28N01). Another exemplary clinician-location metric includes an average time duration (e.g., average of 45 minutes) spent by the clinician in the patient-care space (e.g., patient room 28N01) during each instance in which the RTLS detected a presence of the clinician in the patient-care space. A further exemplary clinician-location metric includes a total amount of time spent by the clinician in the patient-care space within a time interval during which the clinician was assigned to provide care to the patient. Yet another clinician-location metric might indicate a specialization or type of a clinician that is detected in a patient-care space. These clinician-location metrics are determinable from RTLS events 234.

Step 1016 includes receiving the clinician-location metric that describes one or more instances at which a healthcare clinician was present in a patient-care space in which the patient is receiving care. For example, calculator 224 might receive the metric from datastore 212. At step 1018, the clinician-location metric is applied in an algorithm to calculate the resource-consumption score. For example, calculator 224 might apply the clinician-location metric in an algorithm. Once the resource-consumption score is calculated, it can be presented to a user of client terminal 210, such as depicted in FIG. 4 by screen shot 410. That is, screen shot 410 depicts resource-consumption score 424 in a box that includes information relevant to a particular patient named "Tom Fryer." The resource-consumption score provides contextual information that is relevant to assigning a clinician as a provider of a patient.

Figure 10:
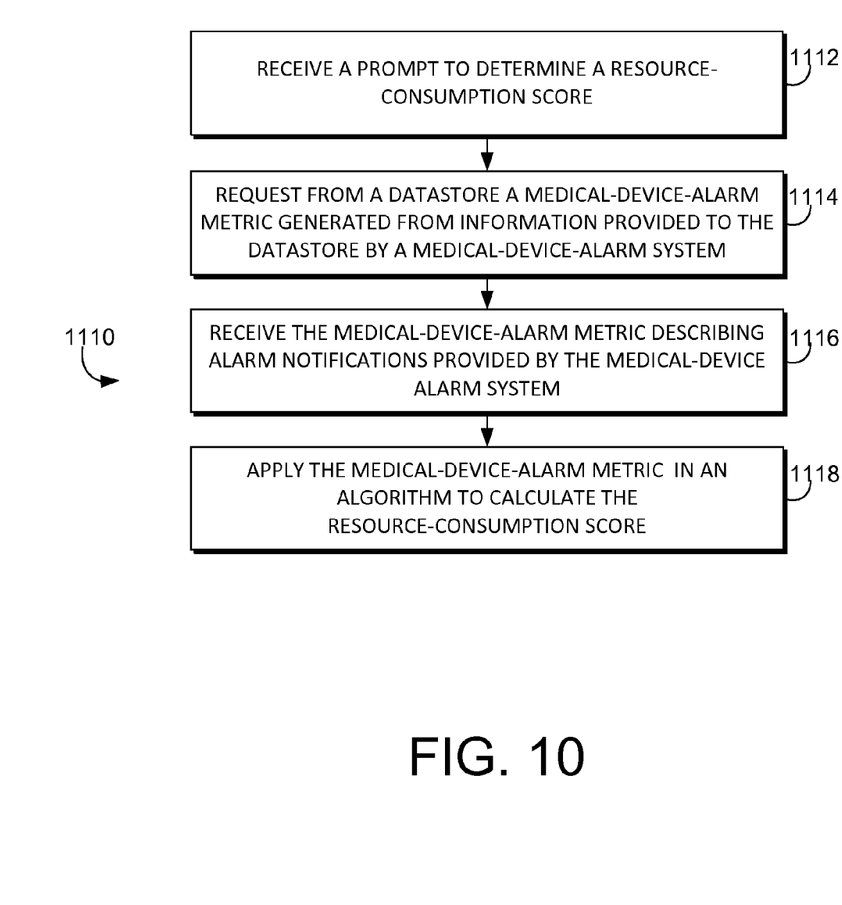

Referring now to FIG. 10, another flow diagram is depicted that presents a method 1110 of determining a resource-consumption score. The steps depicted in FIG. 10 might include computer-executable instructions that, when executed by a computing device, facilitate method 1110. For example, the computer-executable instructions might be stored on computer-readable media and executed using application 270. When describing FIG. 10, reference might also be made to FIGS. 2 and 4.

Method 1110 includes at step 1112, receiving a prompt to determine the resource-consumption score. Various exemplary prompts were described with respect to method 1010, such as a prompt from clinician assignor 222, a direct user request, and a time-interval-based prompt. As such, a prompt may be automatically generated and automatically received when a clinician-assignment application is executed by a computing device. Accordingly, the resource-consumption score may be presented using the computing device when the clinician-assignment application is used to assign a subsequently scheduled clinician to provide care to a patient. Step 1114 includes requesting from a datastore a medical-device-alarm metric that is generated from information provided to the datastore by a medical-device alarm system. For example, calculator 224 might send a request to datastore 212, and more specifically to medical-device events 228, to send medical-device-alarm metrics. As already described, information in medical-device events 228 is received from medical-device-monitoring system 248.

A medical-device-alarm metric can provide various insights into the quantity and quality of alarms triggered in connection with a patient. For example, one medical-device-alarm metric might include an alarm count, which indicates a number of alarm notifications received from the medical-device alarm system. An alarm count might indicate a number of alarm notifications received in a specified duration (e.g., 1 hour or during a shift). Another medical-device-alarm metric might include an alarm-notification type, which indicates a respective severity level of each alarm notification. For example, an alarm notification might be rated to include a low importance, medium importance, or high importance. A further exemplary medical-device-alarm metric might include a device type (e.g., ventilator) that describes a medical device providing the one or more alarm notifications. Each of these metrics provides insight into the amount of resources (e.g., clinician time) that might be needed to provide care to a patient in an upcoming shift. For example, a higher alarm count of a patient might suggest that providing care to the patient consumes more resources. As another example, certain alarm types that are more severe might suggest that providing care to a patient consumes more resources.

At step 1116, the medical-device-alarm metric is received that describes one or more alarm notifications provided by the medical-device alarm system. For example, calculator 224 might receive the metric from datastore 212. At step 1118, the medical-device-alarm metric is applied in an algorithm to calculate the resource-consumption score. For example, calculator 224 might apply the medical-device-alarm metric in an algorithm. Once the resource-consumption score is calculated, it can be presented to a user of client terminal 210, such as depicted in FIG. 4 by screen shot 410. That is, screen shot 410 depicts resource-consumption score 424 in a box that includes information relevant to a particular patient named "Tom Fryer." The resource consumption score provides contextual information that is relevant to assigning a clinician as a provider to a patient.

Although descriptions of methods 1010 and 1110 are related to RTLS events and medical-device events, other information may also be used to determine a resource-consumption score. For example, nurse-call events 236, patient-content events 230, and other information may be retrieved from datastore 212 or from other sources. Nurse-call events 236 may be used in various manners to assess or calculate a resource-consumption score. For example, a quantity of nurse-call events within a given amount of time (e.g., the previous shift) may be used to calculate a resource-consumption score, such that a higher number of events results in a higher score. In addition, a quality of nurse-call events may be used to calculate a resource-consumption score. For example, a higher score may be calculated when nurse-call events are more severe or critical, or are more time consuming to answer. Patient-content events 230 may also be used in various manners to assess or calculate a resource-consumption score. For example, a negative review of a clinician that is submitted by a patient may result in a higher resource-consumption score. These are merely examples, and a variety of different types of information may be used to calculate a resources-consumption score.

As a result of the information provided by various components of FIG. 2, by leveraging the environment depicted in FIG. 2, a user can be more educated when assigning a clinician to a patient as either a primary provider or a secondary provider and can assign a communications device to a clinician. In addition, provider status can be made available to other systems by sending the status to an event repository. Provider status is useful to other systems to provide additional functionality, such as when a communications system is trying to contact a healthcare provider.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A clinician-assignment system comprising:
   a set of healthcare-unit barcodes that are attachable to a display board in a physical arrangement that depicts a floor plan of a healthcare unit;
   a set of one or more clinician barcodes that are attachable to the display board within the physical arrangement, which depicts the floor plan of the healthcare unit;
   a digital camera that records a digital image of the physical arrangement and the set of one or more clinician barcodes, wherein the digital image includes a depiction of the physical arrangement of the set of healthcare-unit barcodes and a depiction of a clinician barcode among the set of healthcare-unit barcodes;
   a barcode-reading application that uses a processor to:
   scan the clinician barcode to determine that the clinician barcode represents a clinician identifier of the clinician;
   determine a position of the clinician barcode in the digital image;
   determine that the position of the clinician barcode is proximate to a healthcare-area barcode included among the healthcare-unit barcodes, wherein the healthcare-area barcode represents a patient room included in the healthcare unit; and
   a clinician-assignment application that uses a processor to create a clinician-assignment data item that codifies an assignment of the clinician identifier to the patient room, to a patient identifier associated with the patient room, or a combination thereof when the clinician barcode is proximate to the healthcare-area barcode.

2. The system of claim 1, wherein each barcode of the set of healthcare-unit barcodes includes an attachment mechanism for attachment to the display board.

3. The system of claim 1, wherein each barcode of the set of healthcare-unit barcodes includes a magnet that magnetically attaches to the display board.

4. The system of claim 1, wherein each barcode of the set of one or more clinician barcodes includes an attachment mechanism for attachment to the display board.

5. The system of claim 1, wherein each barcode of the set of one or more clinician barcodes includes a magnet that magnetically attaches to the display board.

* * * * *